(12) United States Patent
Bak-Boychuk et al.

(10) Patent No.: US 11,759,226 B2
(45) Date of Patent: Sep. 19, 2023

(54) BICUSPID VALVE DISSECTION DEVICE

(71) Applicant: Edwards Lifesciences Corporation, Irvine, CA (US)

(72) Inventors: Gregory Bak-Boychuk, San Clemente, CA (US); Ming H. Wu, Tustin, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 327 days.

(21) Appl. No.: 16/941,168

(22) Filed: Jul. 28, 2020

(65) Prior Publication Data

US 2020/0352694 A1    Nov. 12, 2020

Related U.S. Application Data (62) Division of application No. 16/045,116, filed on Jul. 25, 2018, now Pat. No. 10,765,503.
(Continued)

(51) Int. Cl.
  *A61F 2/01* (2006.01)
  *A61B 17/32* (2006.01)
  (Continued)

(52) U.S. Cl.
  CPC .. *A61B 17/320016* (2013.01); *A61B 17/3201* (2013.01); *A61B 17/320758* (2013.01); *A61B 18/1492* (2013.01); *A61F 2/013* (2013.01); *A61F 2/2412* (2013.01); *A61F 2/2427* (2013.01); *A61F 2/2433* (2013.01);
  (Continued)

(58) Field of Classification Search
  CPC .... A61F 2/01; A61F 2/24; A61F 2/013; A61F 2/2412; A61F 2/2427; A61F 2/2433; A61B 17/3207; A61B 17/3201; A61B 17/32; A61B 17/320758; A61B 17/320016; A61B 18/14
  See application file for complete search history.

(56) References Cited

U.S. PATENT DOCUMENTS 3,574,865 A * 4/1971 Hamaker ............... A61F 2/2409
                                                                623/2.34
4,493,321 A    1/1985 Leather
(Continued)

FOREIGN PATENT DOCUMENTS

CN    102834072 A    12/2012
FR    2903292 A1    1/2008
(Continued)

*Primary Examiner* — Vi X Nguyen
(74) *Attorney, Agent, or Firm* — Guy L. Cumberbatch; Sean Seung Kyu Kim (57) ABSTRACT

The invention is a device, system, and method for repairing heart valve function, which may include bisecting native valve leaflets for improved deployment of a prosthetic heart valve in the native valve annulus. The invention may include a catheter having a cutting element shaft with a cutting element configured to puncture a valve leaflet and/or make a controlled cut through the leaflet. The device may have an extendable foot configured to be positioned on an opposite side of the valve leaflet from the cutting element shaft. The device may include magnets to guide the cutting element and/or cutting element shaft in proper alignment with the extendable foot and to hold the elements in place during leaflet bisection.

15 Claims, 11 Drawing Sheets

Related U.S. Application Data (60) Provisional application No. 62/538,976, filed on Jul. 31, 2017.

(51) Int. Cl.
```
A61B 17/3207   (2006.01)
A61B 18/14     (2006.01)
A61B 17/3201   (2006.01)
A61F 2/24      (2006.01)
A61B 17/00     (2006.01)
A61B 18/00     (2006.01)
A61B 17/22     (2006.01)
A61B 17/3209   (2006.01)
A61B 18/08     (2006.01)
```

(52) U.S. Cl.
CPC ..... *A61B 17/22031* (2013.01); *A61B 17/3209* (2013.01); *A61B 18/08* (2013.01); *A61B 2017/00398* (2013.01); *A61B 2017/00783* (2013.01); *A61B 2017/00876* (2013.01); *A61B 2017/320004* (2013.01); *A61B 2018/00369* (2013.01); *A61B 2018/00595* (2013.01); *A61B 2018/00601* (2013.01); *A61F 2/011* (2020.05); *A61F 2002/016* (2013.01)

(56) References Cited

U.S. PATENT DOCUMENTS

| | | | |
|---|---|---|---|
| 4,765,332 A | 8/1988 | Fischell et al. | |
| 5,026,383 A | 6/1991 | Nobles | |
| 5,069,679 A | 12/1991 | Taheri | |
| 5,514,151 A | 5/1996 | Fogarty et al. | |
| 5,658,302 A | 8/1997 | Wicherski et al. | |
| 5,951,576 A * | 9/1999 | Wakabayashi | A61B 17/115 606/151 |
| 5,989,287 A * | 11/1999 | Yang | A61B 17/11 623/1.36 |
| 6,616,661 B2 | 9/2003 | Wellman et al. | |
| 6,746,463 B1 | 6/2004 | Schwartz | |
| 6,939,359 B2 | 9/2005 | Tu et al. | |
| 7,331,972 B1 | 2/2008 | Cox | |
| 8,486,097 B2 | 7/2013 | Mark et al. | |
| 8,491,614 B2 | 7/2013 | LeMaitre et al. | |
| 8,556,921 B2 | 10/2013 | Bliss et al. | |
| 8,979,925 B2 | 3/2015 | Chang et al. | |
| 9,107,666 B2 | 8/2015 | Manwaring et al. | |
| 9,364,255 B2 | 6/2016 | Weber | |
| 9,402,986 B2 | 8/2016 | Bell et al. | |
| 2004/0243211 A1 | 12/2004 | Colliou et al. | |
| 2005/0137690 A1 | 6/2005 | Salahieh et al. | |
| 2005/0137700 A1 | 6/2005 | Spence et al. | |
| 2006/0095025 A1 | 5/2006 | Levine et al. | |
| 2006/0259137 A1 * | 11/2006 | Artof | A61F 2/243 623/2.11 |
| 2009/0209955 A1 | 8/2009 | Forster et al. | |
| 2012/0209377 A1 | 8/2012 | Machold et al. | |
| 2013/0096606 A1 | 4/2013 | Bruchman et al. | |
| 2013/0116715 A1 | 5/2013 | Weber | |
| 2014/0012252 A1 | 1/2014 | Bliss et al. | |
| 2014/0330366 A1 | 11/2014 | Dehdashtian et al. | |
| 2015/0257883 A1 | 9/2015 | Basude et al. | |
| 2016/0166243 A1 | 6/2016 | Wilson et al. | |

FOREIGN PATENT DOCUMENTS

| | | |
|---|---|---|
| JP | 2008538937 A | 11/2008 |
| JP | 2014534874 A | 12/2014 |
| JP | 2019503232 A | 2/2019 |
| WO | 2009155561 A2 | 12/2009 |
| WO | 2014114798 A1 | 7/2014 |
| WO | 2017074719 A1 | 5/2017 |

* cited by examiner

BICUSPID VALVE DISSECTION DEVICE

CROSS-REFERENCE TO RELATED APPLICATIONS

This application claims the benefit of U.S. Provisional Patent Application No. 62/538,976, filed Jul. 31, 2017, and U.S. patent application Ser. No. 16/045,116, filed Jul. 25, 2018, both of which are incorporated herein by reference in their entireties.

FIELD OF THE INVENTION

The present invention relates to the repair and/or replacement of heart valves, and, more particularly, to methods and apparatuses for the bisection of heart valve leaflets using a catheter with a cutting element.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic, tricuspid, and pulmonary valves usually have three leaflets, while the mitral valve usually has two leaflets.

The operation of the heart, and thus the patient's health, may be seriously impaired if any of the heart valves is not functioning properly. Various problems can develop with heart valves for a number of clinical reasons. Stenosis in heart valves is a condition in which the valves do not open properly. Insufficiency is a condition which a valve does not close properly. Repair or replacement of the aortic or mitral valves are most common because they reside in the left side of the heart where pressures and stresses are the greatest. In a valve replacement operation, a replacement prosthetic valve is implanted into the native valve annulus, which may involve excision of the native valve leaflets.

Heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation. Common examples of such regurgitation include mitral valve regurgitation (i.e., leakage of blood through the mitral valve and back into the left atrium) and aortic valve regurgitation (i.e., leakage through the aortic valve back into the left ventricle). Regurgitation may seriously impair the function of the heart because more blood will have to be pumped through the regurgitating valve to maintain adequate circulation. In early stages, heart valve regurgitation leaves a person fatigued and short of breath. If left unchecked, the problem can lead to congestive heart failure, arrhythmias, or death.

Heart valve regurgitation may be caused by changes in the shape of the heart valve annulus, damage to one or more heart leaflets, and/or damage to the chordae tendinae. In such regurgitation, the heart valve leaflets no longer coapt together properly to seal the valve, so that instead of the leaflets coapting to fully close the valve annulus during systole, an opening remains between the edges of the leaflets.

Dysfunctional heart valves, such as those where the leaflets no longer coapt for proper sealing during systole, can be repaired or replaced with prosthetic devices such as prosthetic valves. In some cases, it may be desirable to remove native structures such as valve leaflets in order for the prosthetic valve to be properly implanted within the native valve annulus. For example, in traditional open-heart surgical procedures, a surgeon uses a scalpel to manually cut native heart valve leaflets. In some cases, a replacement valve can be installed directly over a native valve, without the need to remove or cut native structures such as valve leaflets. For example, in transcatheter aortic valve replacement (TAVR) procedures, the prosthetic valve is delivered through a catheter and deployed within the native valve annulus by pushing native leaflets to the side. In some cases, it may be desirable to cut (e.g., bisect) native leaflets in order for the prosthetic valve to be properly deployed within the native valve annulus. Examples of situations where native leaflet bisection may be desirable include situations where native valve leaflets are deforming (or will deform) the prosthetic valve into an undesirable shape (e.g., deforming the prosthetic valve into an oval shape). For example, a heavily calcified native valve leaflet may have portions that combine to distort the prosthetic valve deployed in the annulus.

Another situation where native leaflet bisection may be desirable is for so-called bicuspid aortic valves (BAVs). In BAVs, an aortic valve has only two (2) leaflets (as opposed to the usual three (3) leaflets), or has adjacent leaflets that are fused (e.g., in edge-to-edge alignment along a raphe/fusion between adjacent leaflets) into a single leaflet structure so that the valve only has two (2) or even one (1) effective leaflet. Prior to deployment of a prosthetic valve in such a valve, it may be desirable to bisect a leaflet into two separate leaflet structures, or to separate two fused leaflets (such as by bisecting the fused leaflets along the raphe).

Various devices and methods are known in the art for valve leaflet dissection and removal. For catheter-based valve leaflet dissection, cutting devices are known that can be delivered via a catheter.

In cases where valve leaflet bisection is desirable to facilitate valve repairs and replacements, traditional cutting devices may have difficulty in advancing a cutting element through a leaflet (e.g., due to the tough tissue/deposit materials often associated with damaged valve leaflets, such as calcified valve leaflets).

There is presently a need for an improved means for performing heart valve repairs and replacements. The current invention fulfills this need.

SUMMARY OF THE INVENTION

The present invention provides a number of devices and methods for cutting (e.g., bisecting) valve leaflets. The devices and methods herein provide the ability to precisely cut leaflets during percutaneous and other procedures without damaging surrounding tissue.

It should be understood that each of the elements disclosed herein can be used with any and all of the elements disclosed herein, even though the specific combination of elements may not be explicitly shown in the figures herein. In other words, based on the explanation of the particular device, one of skill in the art should have little trouble combining the features of certain of two such devices. Therefore, it should be understood that many of the elements are interchangeable, and the invention covers all permutations thereof.

The devices of the present invention can be utilized in standard open surgical procedures, minimally invasive procedures, or percutaneous procedures. In one embodiment the devices can be delivered transapically through a small chest incision. In another embodiment, the devices can be introduced transatrially through an incision performed over the roof of the left or right atrium. In yet another embodiment the devices can be delivered into the left or right ventricle through the chest via a thorascope, which may be performed transapically. The devices can also be delivered percutaneously, such as via a catheter or catheters into the patient's arterial system (e.g., through the femoral or brachial arteries).

Advantages of the device include a low delivery profile, which is conducive to minimally invasive and percutaneous delivery methods. The device is configured to interact properly with the native leaflets for cutting thereof, while minimally interfering with surrounding tissue such as the ventricle, atrial, and subvalvular assemblies.

Embodiments of the present disclosure provide devices and methods for cutting valve leaflets, such as in an aortic valve or a mitral valve. The devices and methods disclosed herein are desirably delivered into a subject's heart using percutaneous or minimally invasive surgical methods. Accordingly, desirable methods described herein may not require extracorporeal circulation (e.g., blood from a subject's circulation being routed outside the body to have a process applied to and then returned to the subject's circulation). For example, in one embodiment, an excision catheter (or similar device) is inserted through an incision in the chest wall and then through the cardiac tissue (e.g., through the apex of the heart) into a chamber of the patient's beating heart. Because such methods may not require extracorporeal circulation, complications can be greatly reduced as compared with traditional open-heart surgery.

A device according to an embodiment of the invention has a steerable catheter shaft, a foot sheath slidingly disposed within the steerable catheter shaft, and a foot element at a distal end of the foot sheath, with the foot element configured to engage a valve leaflet from below the leaflet. The foot element may have a foot opening. A cutting element sheath may be slidingly disposed within the steerable catheter. A cutting element may be selectively extendable from the cutting element sheath distal end and into the foot opening. Alignment magnets (such as selectively activated electromagnets) may be provided in the foot element and/or cutting blade sheath distal end. The foot may be configured when extended distally from the catheter shaft to extend sideways from the foot sheath, and may have an overall length between 0.5 and 2.0 centimeters and/or an overall width between 0.3 and 0.8 centimeters; up to 1.0 cm; up to 1.5 cm; up to 2 cm; 1.0 to 2.0 cm. The foot may self-expand when extended from the catheter shaft, and may be formed from nitinol or similar memory material. Various cutting elements are within the scope of the invention, such as a simple cutting blade; a motor driven rotating rod having an abrasive surface; an electrocautery device; a curved blade; and/or scissors. The device may include an embolic filter configured to be extended from the steerable catheter.

A system for treating a heart valve according to an embodiment of the invention may have a device for bisecting native heart valves; a delivery catheter for delivering a prosthetic heart valve, with the delivery catheter comprising a flexible elongated delivery shaft with a delivery shaft distal end, the delivery catheter further comprising a prosthetic heart valve holding portion on the delivery shaft distal end; and a radially expandable prosthetic heart valve. The radially expandable prosthetic heart valve may be held by the prosthetic heart valve holding portion of the delivery catheter. The prosthetic heart valve may be radially expandable, such as radially self-expanding or balloon expandable. The delivery catheter may be a balloon catheter with an expandable balloon at the delivery shaft distal end.

A method for bisecting heart valve leaflets according to the invention may involve advancing a steerable catheter shaft through anatomy of the patient to a position near a native heart valve having a valve annulus, advancing a foot out of the steerable catheter shaft and distally past a valve leaflet of the native heart valve; positioning the foot against a distal side of the valve leaflet; advancing a cutter sheath out of the steerable catheter shaft, the cutter sheath comprising a cutter sheath distal end; positioning the cutter sheath distal end against a proximal side of the valve leaflet; holding the valve leaflet between the foot and the distal end of the cutter sheath; and advancing a cutting element out of the cutter sheath and into the valve leaflet at a selected entry position on the valve leaflet. The cutting element may be moved across the valve leaflet to create a cut extending across at least a portion of the valve leaflet. The selected entry position in the valve leaflet may be adjacent the valve annulus, and moving the cutting element across the valve leaflet may involve moving the cutting element from the selected entry position adjacent the valve annulus to a free edge of the valve leaflet such that the cut extends from the desired entry position to the free edge. Alternatively, the entry point can be a location along the free edge and the cutting advances along a selected path into the valve leaflet. Where the valve leaflet has calcified deposits, moving the cutting element across the valve leaflet may involve avoiding contact between the cutting element and the calcified deposits such that the cut do not dislodge the calcified deposits. The cutter sheath distal end may have a first magnet and the foot may have a second magnet, and positioning the cutter sheath distal end against the proximal side of the valve leaflet may involve aligning the first magnet with the second magnet via the magnet attraction forces of the respective magnets. At least one of the first magnet or second magnet may be a selectively activated electromagnet, and positioning the cutter sheath distal end against the proximal side of the valve leaflet may involve activating the electromagnet.

Various valves can be treated using the devices and methods of the invention, including aortic, mitral, tricuspid, and pulmonary valves. The specific approach for advancement of a device through the patient's anatomy may depend on the particular valve being treated. For example, for an aortic valve the approach may involve advancing the steerable catheter shaft through the patient's anatomy to the position near the native heart valve, including advancing the steerable catheter shaft through a femoral artery and into an aorta and around an aortic arch of the patient.

The invention may include one or more embolic filtering elements. For example, prior to advancing a cutting element out of the cutter sheath and into the valve leaflet, an embolic filter may be deployed from the steerable catheter shaft and into a position such that substantially all blood flowing past the valve leaflet passes through the embolic filter prior to passing through lungs or brain of the patient.

The device may be delivered using various approaches, including percutaneously or transapically through the subject's vasculature.

Other objects, features, and advantages of the present invention will become apparent from a consideration of the following detailed description.

BRIEF DESCRIPTION OF THE DRAWINGS

FIGS. 3A-3E depict top views of heart valves after treatment according to embodiments of the invention;

DETAILED DESCRIPTION OF SEVERAL EMBODIMENTS

Figure 1:
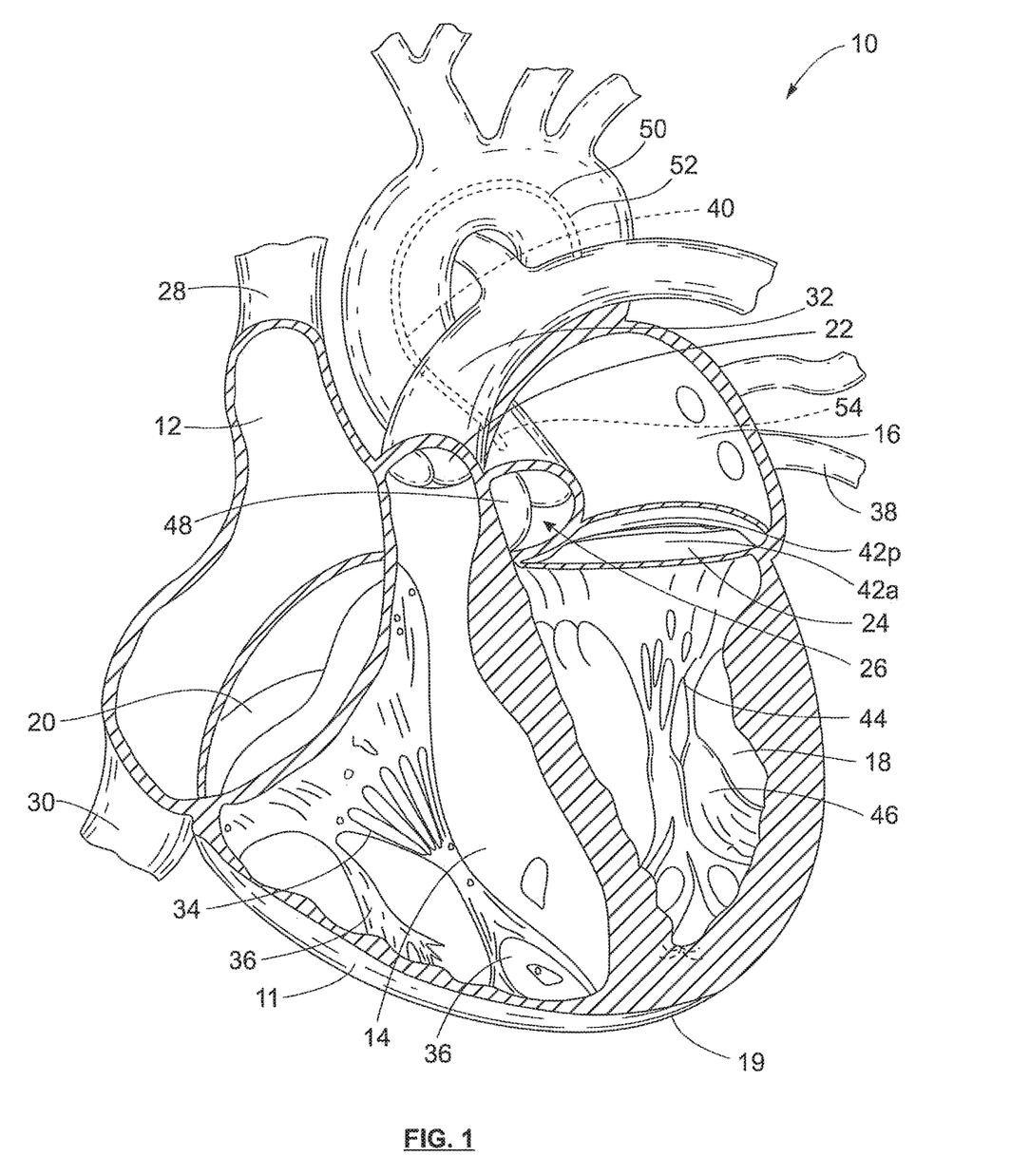
FIG. 1 is a cross-sectional view of a heart with a device according to an embodiment of the invention advanced therein.

A cross-sectional view of a human heart 10 is depicted in FIG. 1. The heart 10 has a muscular heart wall 11, an apex 19, and four chambers: right atrium 12; right ventricle 14; left atrium 16; and left ventricle 18. Blood flow is controlled by four main valves: tricuspid valve 20; pulmonary valve 22; mitral valve 24; and aortic valve 26. Blood flows through the superior vena cava 28 and the inferior vena cava 30 into the right atrium 12 of the heart 10. The right atrium 12 pumps blood through the tricuspid valve 20 (in an open configuration) and into the right ventricle 14. The right ventricle 14 then pumps blood out through the pulmonary valve 22 and into the pulmonary artery 32 (which branches into arteries leading to the lungs), with the tricuspid valve 20 closed to prevent blood from flowing from the right ventricle 14 back into the right atrium 12. Free edges of leaflets of the tricuspid valve 20 are connected via the right ventricular chordae tendinae 34 to the right ventricular papillary muscles 36 in the right ventricle 14 for controlling the movements of the tricuspid valve 20.

After leaving the lungs, the oxygenated blood flows through the pulmonary veins 38 and enters the left atrium 16 of the heart 10. The mitral valve 24 controls blood flow between the left atrium 16 and the left ventricle 18. The mitral valve 24 is closed during ventricular systole when blood is ejected from the left ventricle 18 into the aorta 40. Thereafter, the mitral valve 24 is opened to refill the left ventricle 18 with blood from the left atrium 16. Free edges of leaflets 42a, 42p of the mitral valve 24 are connected via the left ventricular chordae tendinae 44 to the left ventricular papillary muscles 46 in the left ventricle 18 for controlling the mitral valve 30. Blood from the left ventricle 18 is pumped through the aortic valve 26 into the aorta 40, which branches into arteries leading to all parts of the body except the lungs. The aortic valve 26 includes three leaflets 48 (or two leaflets if the aortic valve is of a bicuspid type) which open and close to control the flow of blood into the aorta 40 from the left ventricle 18 of the heart as it beats. A device 50 according to the invention is depicted with the elongated shaft 52 advanced through the patient's vascular system to position the device distal end 54 adjacent the aortic valve 26 in order to bisect the leaflets 48 thereof.

Figures 2A, 2B, 2C, 2D, 2E:
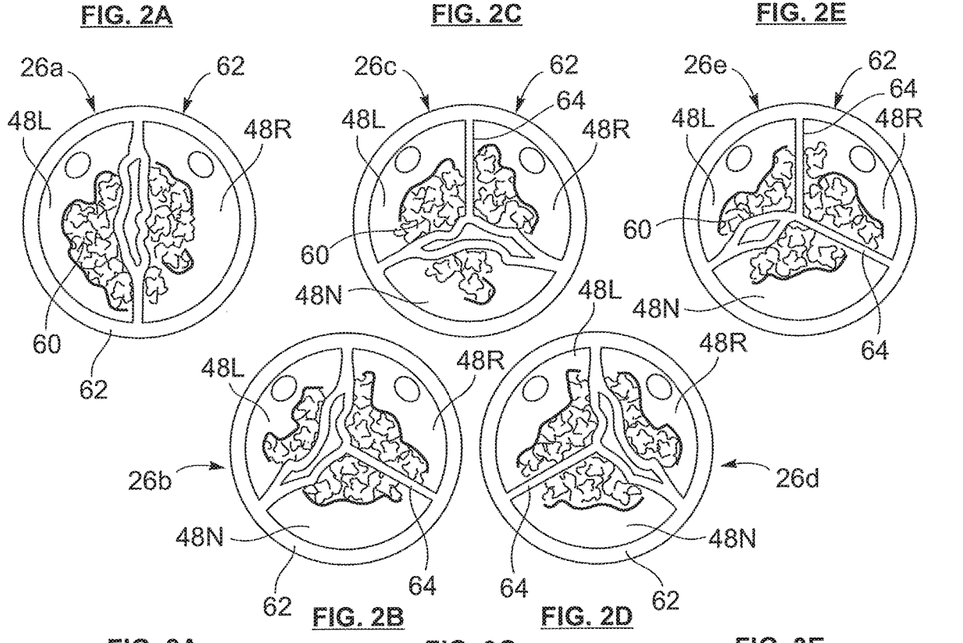
FIGS. 2A-2E depict top views of heart valves prior to treatment according to embodiments of the invention.
Figures 3A, 3B, 3C:
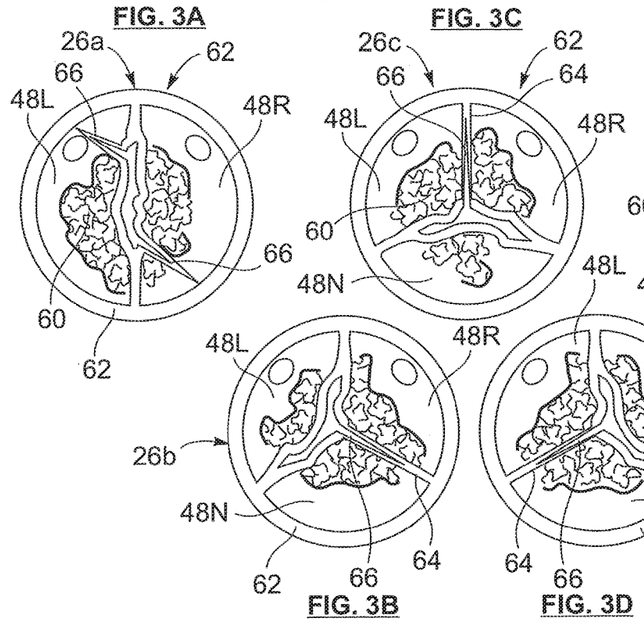
Figure 3E:
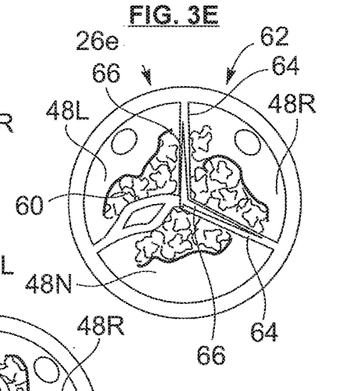

FIGS. 2A-2E depict top views of various defective aortic valves with proposed bisection lines. FIG. 2A depicts a Type 0 bicuspid aortic valve 26a, aka a "purely" bicuspid aortic valve, where there are only two valve leaflets 48L (left), 48R (right) as opposed to the normal three leaflets for an aortic valve. The valve 26a may include calcium deposits 60 which may contribute to valve stenosis/dysfunction. Such an aortic valve 26a may tend to form an oval shape when radially expanded, such as when a prosthetic heart valve is radially expanded within the annulus 62a. FIG. 2B depicts a Type 1 bicuspid aortic valve 26b, where adjacent left and right valve leaflets 48L, 48R are secured at their edges via a raphe 64 but the nonseptal (posterior) leaflet 48N is not fused. FIG. 2C depicts another Type 1 bicuspid aortic valve 26c, where adjacent valve leaflets 48R, 48N are secured at their edges via a raphe 64. FIG. 2D depicts another Type 1 bicuspid aortic valve 26d, where adjacent valve leaflets 48N, 48L are secured at their edges via a raphe 64. FIG. 2E depicts a Type 2 bicuspid aortic valve 26e, where adjacent valve leaflets 48L, 48N, 48R are secured at their edges via multiple raphes 64.

For such bicuspid aortic valves, proper deployment of an expandable transcatheter prosthetic heart valve within the native valve leaflets may prove difficult because the bicuspid valve leaflets may resist the prosthetic heart valve's desired circular expansion within the annulus because the native valve leaflets more strongly resist prosthetic valve expansion at one side or region of the native valve annulus than at other sides/regions. For example, in the purely bicuspid valve 26a of FIG. 2A, the leaflets 48L, 48R will more strongly resist prosthetic valve expansion than the commissure portions of the native valve 26a, so that a prosthetic valve deployed therein may be forced toward an oval shape by the native leaflets 48L, 48R as opposed to a desired circular shape.

By cutting one or more bisection cuts through one or more of the native leaflets, the tendency of the native leaflets to deform the native valve annulus and/or resist proper circular expansion of a prosthetic heart valve therein may be substantially reduced.

Such bisection cuts may preferably be made so as to prevent embolization of leaflet tissue, such as by avoiding calcified regions and by avoiding cuts that will result in leaflet tissue being cut free of the native valve. The particular cutting paths may preferably be selected by the user (e.g., physician) based on the desired outcome and the particular native valve structure, with the purpose of avoiding embolization of native valve leaflet tissue. FIGS. 3A-3E depict top views of heart valves with bisecting cuts 66 made therein according to embodiments of the invention. The bisecting cuts 66 may preferably pass from a portion of the leaflet adjacent the valve annulus and then out of the leaflet at a position toward the center of the valve annulus. Note that in some cases where adjacent leaflets are fused at raphes the bisection cuts 66 may be made along, or parallel to, the raphes 64. The bisecting cuts effectively increase the number of leaflets by bisecting individual leaflets (FIG. 3A) or two conjoined leaflets (FIGS. 3B-3D) or three conjoined leaflets (FIG. 3E) into two or more separate leaflet structures.

Figure 4A:
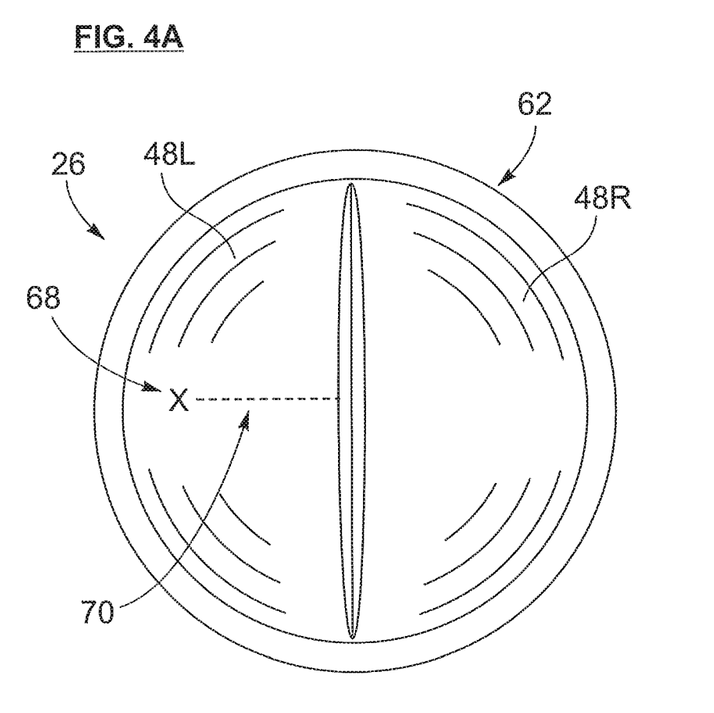
FIGS. 4A-4B depict top views of a heart valve before and after treatment according to an embodiment of the invention.
Figure 4B:
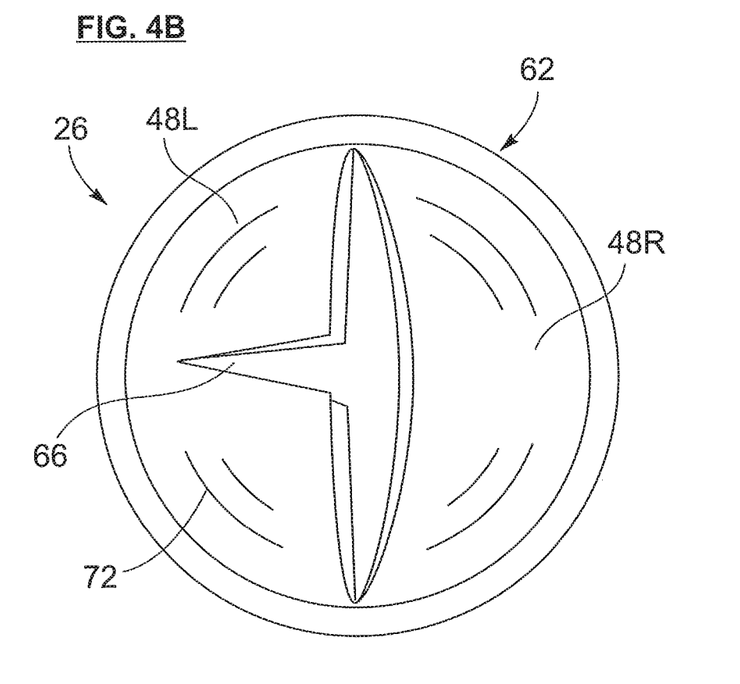

FIGS. 4A and 4B depict a cutting method according to an embodiment of the invention. As depicted in FIG. 4A, an initial puncture 68 can be made adjacent the valve annulus 62, and then follow a cutting path 70 toward the leaflet free edge and the center of the valve opening. The result is that the left leaflet 48L is bisected by the cut 66 into two separate leaflet structures 72, as depicted in FIG. 4B.

A device 50 according to the invention is depicted in FIGS. 5A-5D, having an elongated steerable sheath 52, distal end 54, and proximal end 56. The device 50 has a cutting blade sheath 78 with a cutting blade member 80 slidingly disposed therein. The cutting blade sheath 78 and a foot shaft 82 are slidingly disposed in the steerable outer sheath 52. The cutting blade sheath 78, cutting blade member 80, and foot shaft 82 are configured to be moved distally and proximally with respect to each other. A control handle 84 at the proximal end 56 includes various controls, such as steering controls 86 to steer the steerable sheath, sliding controls 88, 90 configured to advanced and retract the cutting blade sheath 78 and foot shaft 82, and a blade control 91 configured to advance and retract the blade 92 via the blade member 80.

Figure 5A:
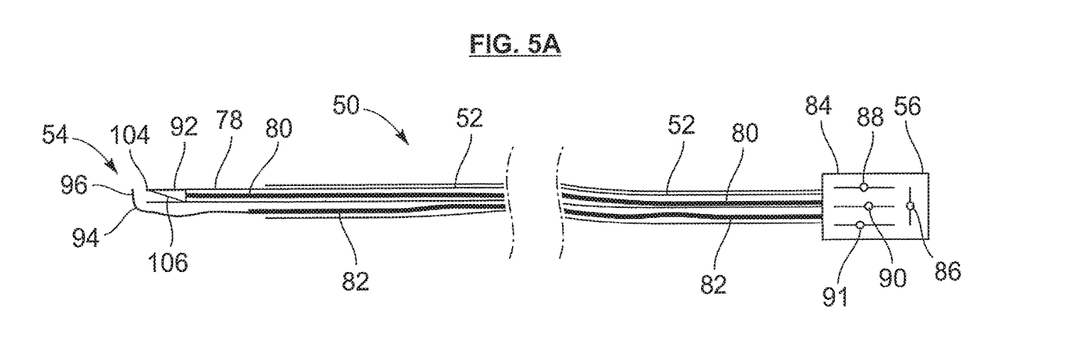
FIGS. 5A-5D depict side, distal end, side (close up), and side (close up) views of a device according to an embodiment of the invention.
Figure 5B:
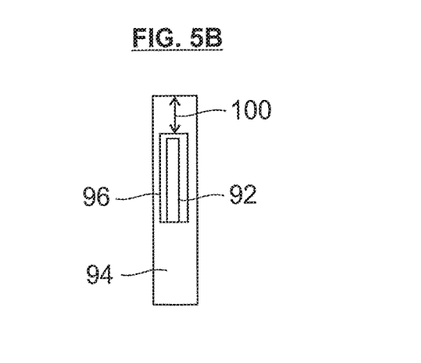
Figure 5C:
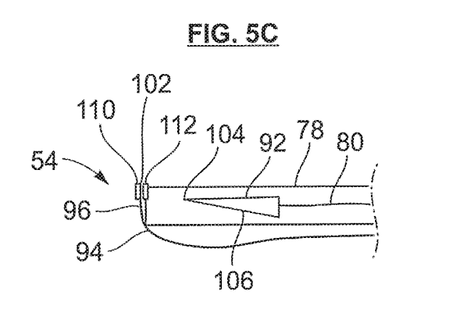
Figure 5D:
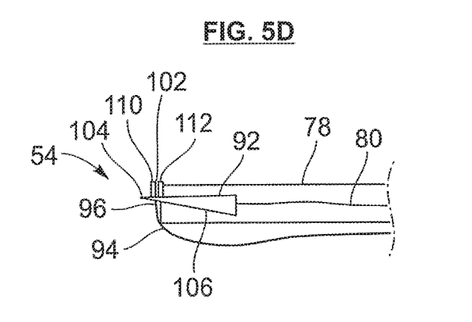

The cutting blade member 80 has a cutting blade 92 at a distal end thereof, and the foot shaft 82 has a foot 94 having a blade-receiving opening 96 at a distal end thereof. As depicted in FIGS. 5A-5C, prior to penetration of the leaflet the cutting blade 92 is proximal of the foot opening 96. In a cutting configuration as depicted in FIG. 5D, the cutting blade 92 is advanced distally with respect to the foot 94 until a portion of the cutting blade 92 is seated in the foot opening 96. Note that in a delivery configuration, the cutting blade sheath 78, cutting blade member 80, cutting blade 92 and foot 94 are retracted within the steerable catheter 52 or are entirely outside patient.

The foot 94 is configured when deployed to extend sideways from the foot shaft 82 in order to extend under a valve leaflet and to support at least a portion of a valve leaflet from a distal side thereof when the device approaches the leaflet from a proximal side thereof. The foot 94 when deployed may have an overall width 95 (e.g., 0.3 and 0.8 cm; 1.0 to 2.0 cm; up to 1.0 cm; up to 1.5 cm; or up to 2 cm), and/or an overall length 97 (e.g., between 0.5 and 2.0 centimeters). The foot 94 may have a distal lip 98 extending beyond the opening 96, with the distal lip 98 spacing the blade 92 a distance 100 (e.g., between 0.1 and 0.5 centimeters) from the distal lip tip 102, which is sufficient to prevent the blade 92 from inadvertently cutting adjacent heart structures, such as aortic and ventricular structures.

The cutting blade 92 has a sharp tip 104 for puncturing tissue and a cutting edge 106 for slicing tissue, with the cutting edge 106 directed toward the foot shaft 82. With the sharp tip 104 driven through a layer of material (such as valve tissue) and also positioned within the foot opening 96, retracting the device 50 away from the layer of material (e.g., by pulling the device proximally from the layer of material) will cause the cutting edge 106 to engage against and cut through the layer of material.

Magnets 110, 112 may be included to assist in guiding the cutting blade sheath 78 and/or cutting blade 92 to proper alignment with the foot 94 and foot opening 96; and/or to hold the distal end of the cutting blade sheath 78 against the foot 94 in order to hold the device to a valve leaflet. One or more magnets may be located on or adjacent the blade or blade sheath, and the blade itself or the blade sheath itself may be magnetic. One or more magnets may be located on or adjacent the foot, and the foot itself may be magnetic. The magnets may be permanent magnets, or may be electromagnets configured to be selectively activated by a user when it is desired to advance and hold the cutting blade sheath 78 in position with the foot 94.

The device may be formed of various materials. For example, the foot 94 and/or blade sheath 78 may be formed from nitinol.

The device 50 may include radiopaque and/or other visualization enhancement elements. For example, radiopaque markers may be included on the blade sheath 78 and/or blade 92 and/or foot 94, such as at or adjacent the locations of the magnets 110, 112.

Various approaches for advancing the device into position for valve leaflet bisection are within the scope of the invention. One preferred approach when treating an aortic valve is a transcatheter approach via a femoral artery. The method may include deployment of a transcatheter aortic valve replacement (TAVR), which may be performed using the same transcatheter approach. For example, a blade bisection catheter such as that disclosed herein may be used to bisect leaflets of a native valve. The cutting procedures may be performed first, followed by deployment of the transcatheter prosthetic valve. While the cutting procedure may reduce the competency of the native valve, the temporary reduction in native valve competency will not be detrimental to the procedure outcome because the transcatheter prosthetic valve will be deployed shortly after valve leaflet bisection.

In one example of a procedure to bisect native valve leaflets according to the invention, femoral artery access is obtained via an access sheath of the type used for TAVR procedures. The access sheath is positioned at the access site. A guide wire is advanced from the femoral access site thru the aortic arch and into the patient's left ventricle. The steerable shaft can be advanced over the guide wire, such as via standard over-the-wire techniques, to advance the distal end of the device to the target location. For example, the device may have a guide wire lumen. Echo and fluoroscopic visualization techniques may be used.

Figure 6A:
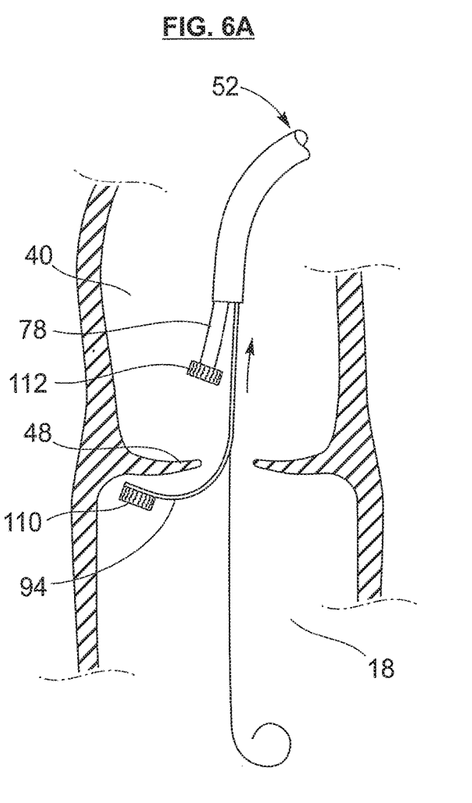
FIGS. 6A-6D depict side (cross-section) views of a heart valve being treated with a device according to an embodiment of the invention.

With the steerable shaft 52 positioned at the target location, the foot 94 is extended distally out of the steerable shaft 52 and into the left ventricle 18 to a position below the aortic valve leaflet 48 to be bisected. The foot 94 is then retracted proximally to engage the valve leaflet 48 from the ventricular side, as depicted in FIG. 6A. Positioning of the foot 94 can be visualized, such as via echo and/or fluoroscopic techniques.

Figure 6B:
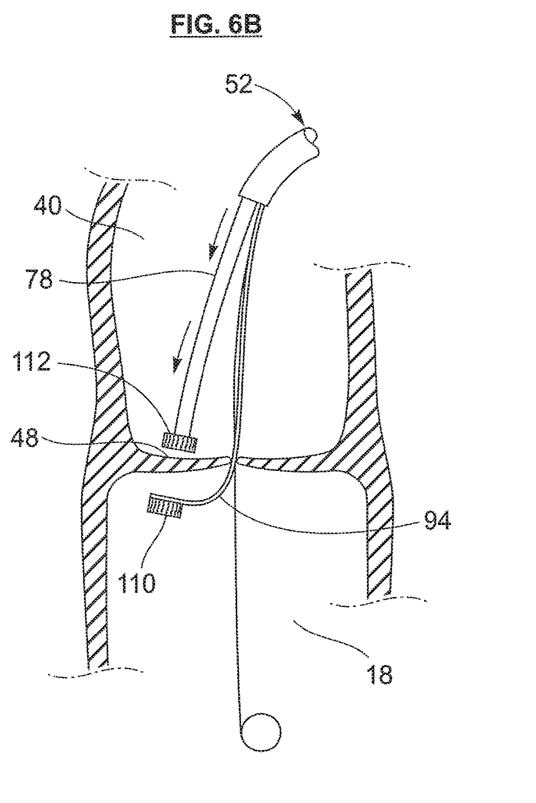
Figure 6C:
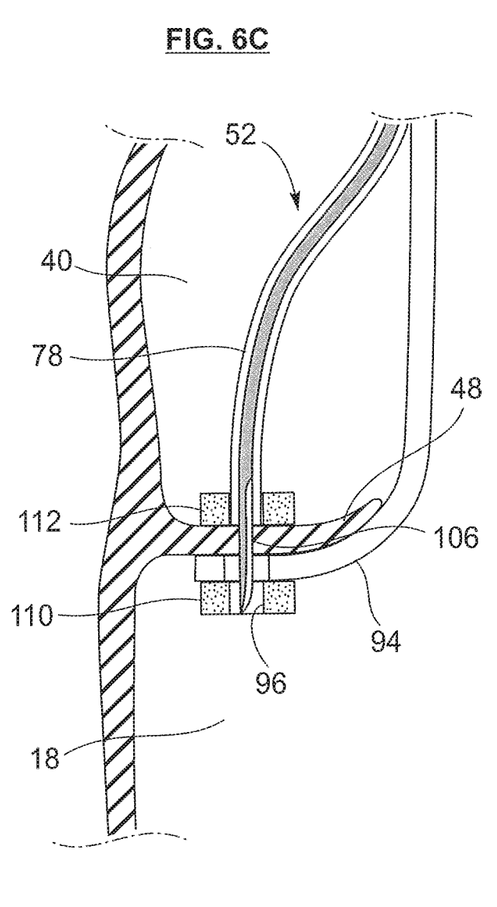
Figure 6D:
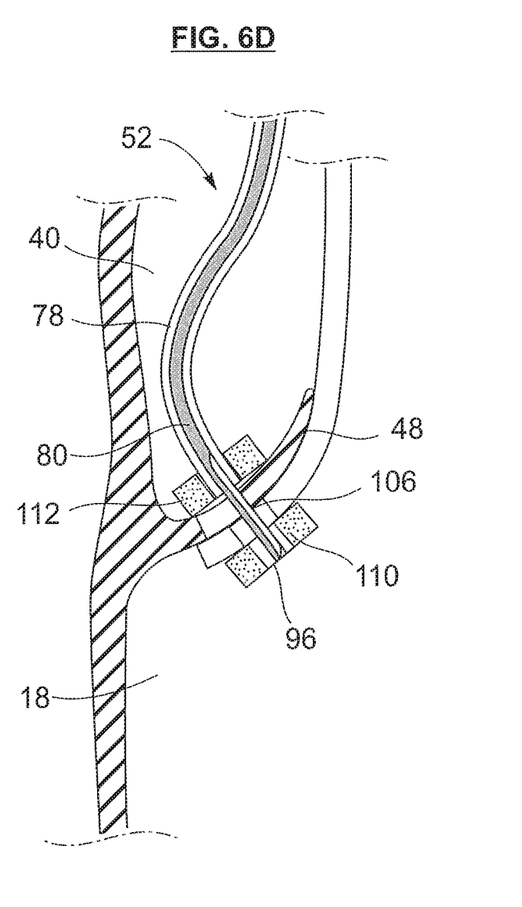
Figure 7A:
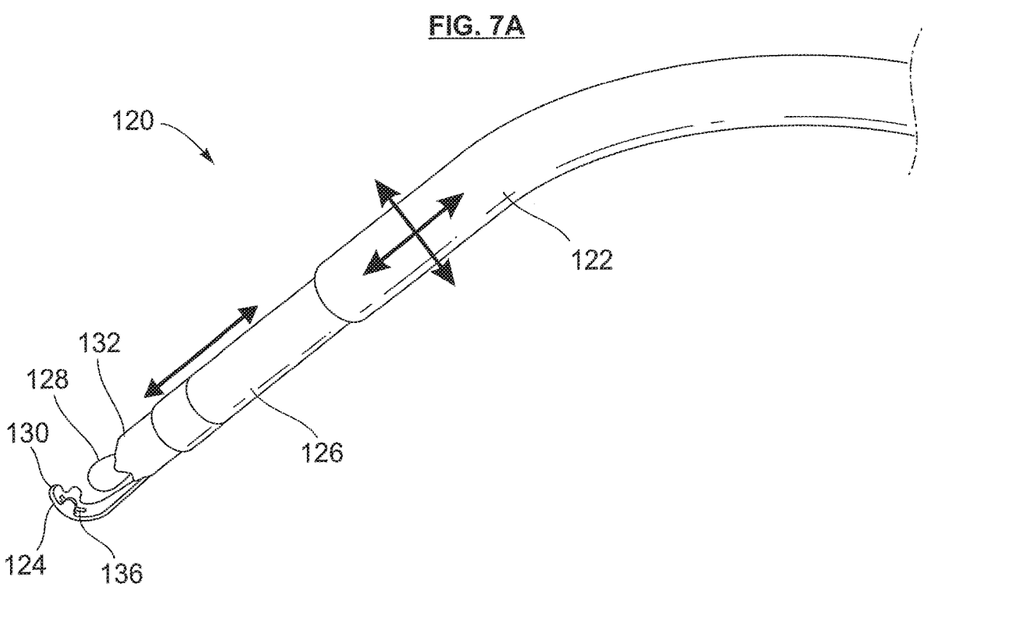
FIGS. 7A-7D depict perspective, side, perspective (close up), and perspective (close up) views of a device according to an embodiment of the invention.
Figure 7B:
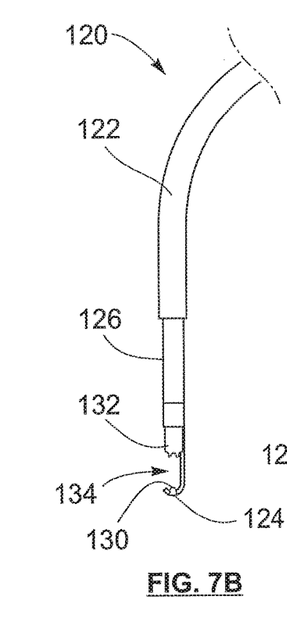
Figures 7C, 7D:
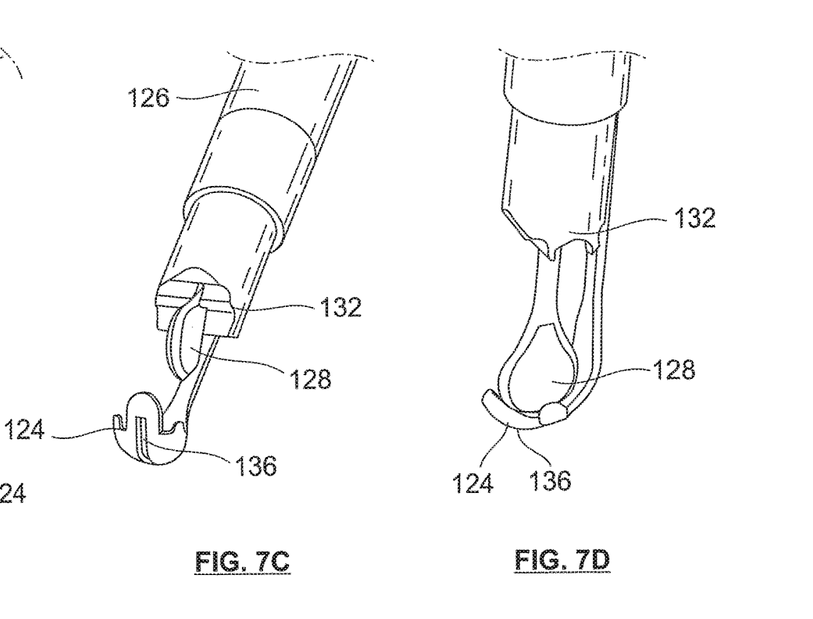

Once proper location of the foot 94 is confirmed, the blade sheath 78 can be advanced distally toward the leaflet 48 and the foot 94, as depicted in FIG. 6B. The magnets 110, 112 help to align the blade sheath 78 with the foot 94. Visualization such as via echo and fluoroscopic techniques may be used to verify alignment of the blade sheath 78 with the foot 94. The blade sheath 78 and foot 94 once aligned can be pressed toward each other to hold the target leaflet 48 therebetween, with the sheath 78 engaging the leaflet 48 from the aortic side and the foot 94 engaging the leaflet 48 from the ventricular side, and with the magnets 110, 112 holding the sheath 78 and foot 94 in their respective positions. Once the alignment and positioning of the sheath 78 and foot 94 is achieved, the blade 92 can be advanced distally from the blade sheath 78 to penetrate the valve leaflet 48 and enter the foot opening 96, as depicted in FIG. 6C. Once the blade 92 is advanced through the leaflet 48 and is secured within the foot opening 96, the foot 94 can be withdrawn proximally, which pulls the blade 92 distally with the blade edge 106 dragged proximally such that the blade edge 106 slices through the valve leaflet 48. The blade sheath 78, blade member 80, and foot 94 may preferably be flexible (which may involve them being formed from nitinol), so that as the foot 94 is withdrawn the pull direction of the blade cutting edge 106 is away from the aortic wall and fairly axial with respect to the aortic valve axis, as depicted in FIG. 6D. The procedure can be repeated for different leaflets, and/or for the same leaflet if multiple cuts are desired in a single leaflet.

An alternative embodiment of a device 120 according to the invention is depicted in FIGS. 7A-7D. The device 120 comprises a steerable catheter 122, a distally extendable foot 124, a blade sheath 126, and a blade 128. The steerable catheter 122 is configured to contain the blade sheath 126, foot 124, and blade 128, all of which can be distally extended from the steerable catheter 122 once the steerable catheter distal end is at the desired treatment location. The foot 124 is configured to be distally extended to a position on the distal side of a valve leaflet, such that a proximal side 130 of the foot 124 is facing toward the distal side of the valve leaflet. The foot 124 can then be retracted until the leaflet is compressed and thereby held between the foot proximal side 130 and the distal end 132 of the steerable catheter 122. The distal end 132 of the steerable catheter may have a gripping surface thereon, as may the proximal side 130 of the foot 124, such that when the two are brought together they form a traction clamp that can physically restrain a valve leaflet therebetween. The foot proximal face 132 and proximal side 130 of the foot 126 may have interlocking surfaces. The foot 124 may have a pocket 134 or other opening configured to receive the blade 128 therein.

Once the leaflet is secured in the traction clamp, the blade 128 can be distally advanced from the blade sheath 126 into the leaflet tissue and into the pocket 134. The blade 128 may be contoured for optimal cutting, and may allow pullback as a cutting method such as previously described for the other embodiments. The blade 128 may have a sharpened cutting edge 136, which may curve around the blade 128 on the bottom and both sides, so that the device 120 can cut both toward and away from the valve leaflet edge. The blade 128 may be manually activated by a user via a sliding control such as those discussed previously, or may be powered (e.g., via electronic motor) for repeated strokes in a sawing action.

Figure 8:
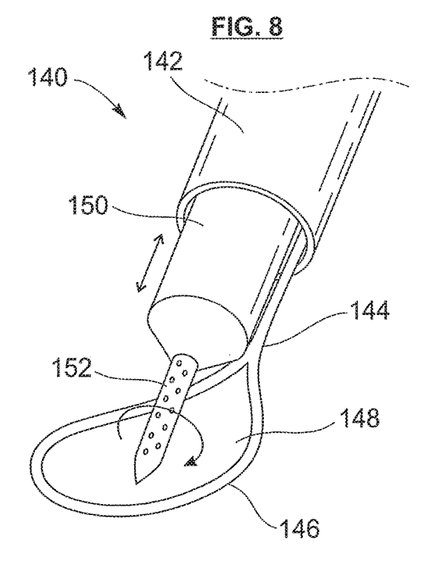
FIG. 8 depicts a perspective view of a device according to an embodiment of the invention.

Another embodiment of a device 140 according to the invention is depicted in FIG. 8. The device 140 has a steerable catheter 142, a foot sheath 144, and a foot 146 with a foot opening 148. A cutter sheath 150 is slidingly extendable from the steerable catheter 142, and has a rotatable cutting element 152 which can be distally advanced and retracted from the cutter sheath 150. The rotatable cutting element 152 may be distally powered by a small electric motor (not shown) or similar power source that can spin the cutting element 152 at high speeds. The cutting element 152 may have an abrasive surface (such as a diamond coating) to improve the cutting capabilities when spun at high speed. With the foot 146 positioned at the far side of a valve leaflet, the cutting element 152 is driven into the leaflet and into the foot opening 148. Note that the motor may be activated to rotate the cutting element 152 either before or after the puncture is created in the valve leaflet. With the motor running and the cutting element 152 spinning, the cutting element 152 is pulled through (and cuts through) the desired cutting path in the leaflet.

Figure 9:
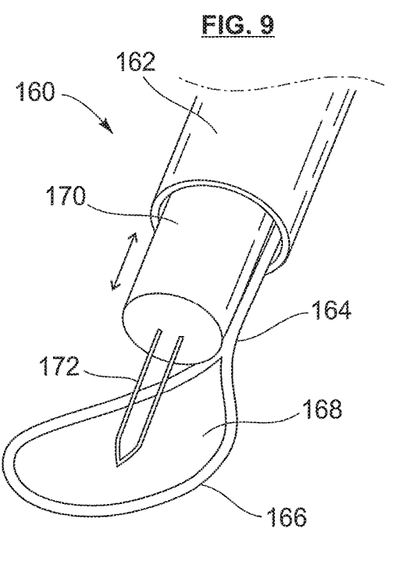
FIG. 9 depicts a perspective view of a device according to an embodiment of the invention.

A further embodiment of a device 160 has a steerable catheter 162, a distally extendable foot sheath 164, and foot 166 with a foot opening 168, as depicted in FIG. 9. A cutter sheath 170 is distally extendable from the steerable catheter 162, and has an electrocautery tip 172 which may be distally extended and retracted from the cutter sheath 170. The electrocautery tip 172 may be powered by DC or AC electrical power sufficient to cut valve leaflet tissue. In use, the foot 166 is positioned on the far side of a valve leaflet. The cutter sheath 170 is advanced to a position on the near side of the valve leaflet, which may involve grasping the leaflet between the foot and cutter sheath distal end. With power provided to the electrocautery tip 172, the tip 172 is driven through the valve leaflet at a desired puncture site. With power applied, the tip 172 is drawn through the valve leaflet, cutting the leaflet along the desired cutting path.

Figures 10, 11:
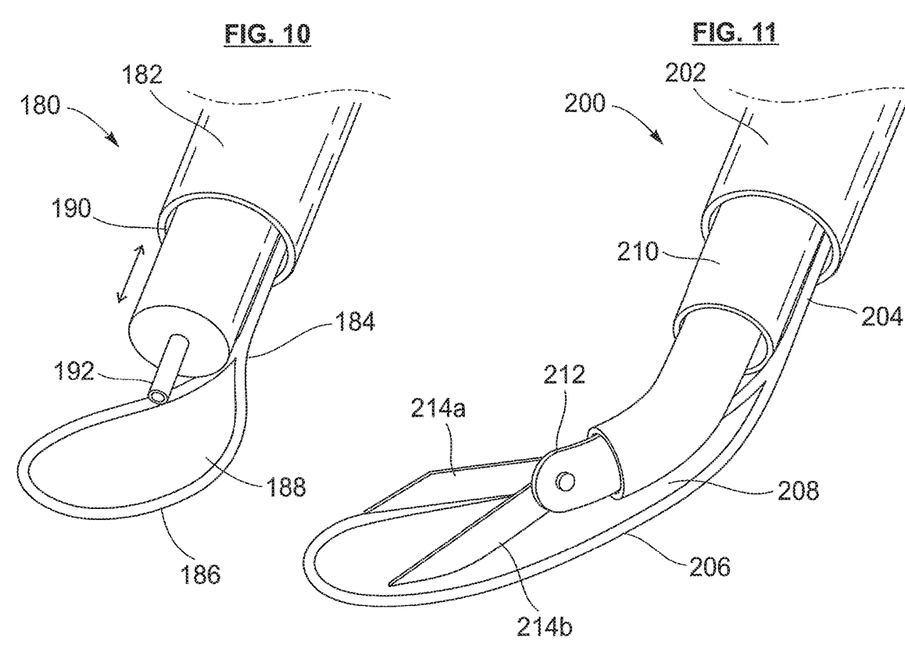
FIG. 10 depicts a perspective view of a device according to an embodiment of the invention.
FIG. 11 depicts a perspective view of a device according to an embodiment of the invention.

FIG. 10 depicts another embodiment of a device 180 according to the invention with a steerable catheter 182. A distally extendable foot sheath 184 has a foot 186 with foot opening 188. The cutter sheath 190 includes a laser cutting element 192, such as a guided laser fiber. Laser energy can be provided from various laser sources, such as a thulium YAG laser.

As depicted in FIG. 11, a device 200 may have a scissor-like cutting element 212. In the example depicted, a foot sheath 204 and cutting sheath 210 are slidingly extendable from a steerable catheter 202. A foot 206 with foot opening 208 can be advanced to the far side of a valve leaflet, and the scissor-like cutting element 212 advanced out of the cutter sheath 190 to cut the valve tissue, with the lower cutting blade 214b extending into the foot opening 208 and below the valve leaflet and the upper cutting blade 214a above the leaflet. The scissor-like cutting element 212 can powered manually (e.g., by operation of elements on the proximal end of the device) or via an electric motor (which may have controls on the proximal end of the device).

Figure 12A:
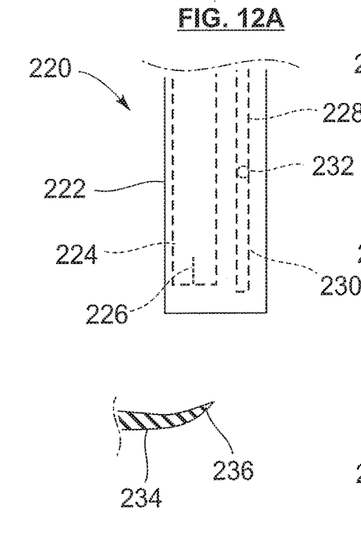
FIGS. 12A-12F depict side, side, top (sectional), side, top (sectional), and side views of a device according to an embodiment of the invention.
Figures 12B, 12C, 12D, 12E:
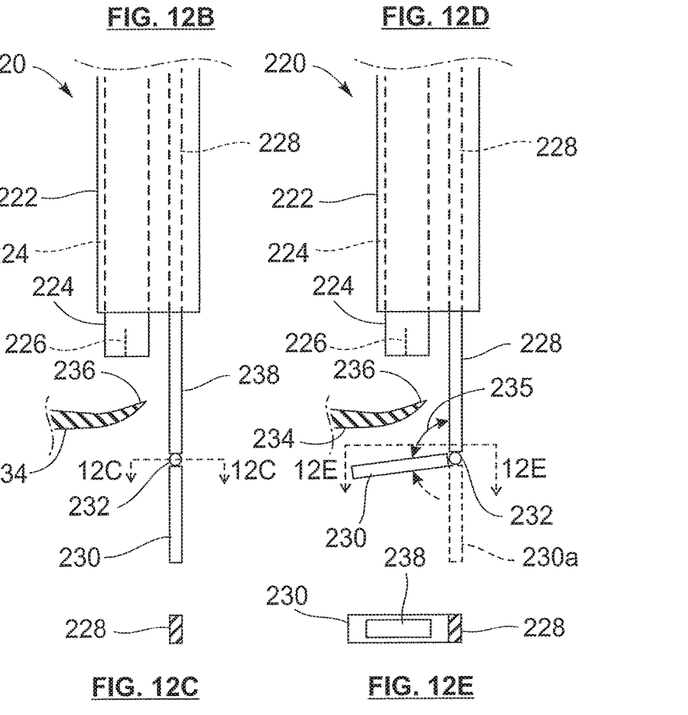
Figure 12F:
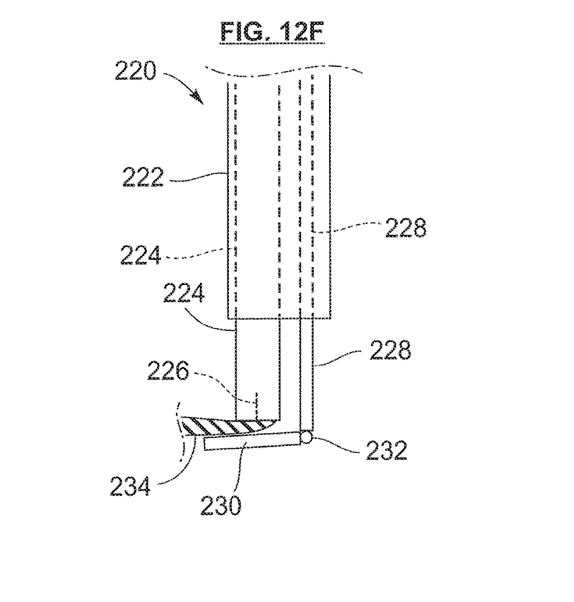

Many variations on foot elements are within the scope of the invention. Foot elements may be configured to be advanced to and past a native heart valve leaflet in a reduced diameter and/or lengthwise configuration in order to better navigate the patient's anatomy, including navigating the space between leaflets. FIGS. 12A-12E depict a device 220 having a steerable catheter 222, a cutting element sheath 224 and cutting element 226, and with a foot base element 230 that can be mechanically manipulated in its configuration. The foot base element 230 secured via a hinge-like connection 234 at a distal end of a flexible elongated foot control rod 228. The foot base element 230 has a foot hole 232 configured to receive the cutting element 226. As depicted in FIG. 12A, the steerable catheter 222 is advanced into the patient's anatomy to a position adjacent a heart valve leaflet 236 to be treated. The base foot element 230 is advanced distally from the steerable catheter 222 in a lengthwise configuration (i.e., aligned with the steerable catheter 222 distal portion) to a position past the valve leaflet edge 238, as shown in FIGS. 12B-12C. The base foot element 230 is then moved, e.g., by rotation about the hinge-like connection 234, to a sideways configuration at a position that is below the valve leaflet 236, as depicted in FIGS. 12D and 12E. Note that in the sideways configuration the foot base element 230 may be at an angle 235 of between 45 and 135 degrees from the distal portion of the elongated foot control rod 228. The foot base element 230 can then be moved proximally (e.g., by proximal retraction of the elongated foot rod 228) and into contact with the distal surface of the valve leaflet 236, and the cutting element sheath 224 can be advanced distally into engagement with the proximal surface of the valve leaflet 236, as depicted in FIG. 12F. The valve leaflet 236 can thus be held between the foot base element 230 and cutting sheath 224. The cutting element 226 can then be moved through the valve leaflet 236 to make the desired cuts.

Note that in other embodiments similar to that of FIGS. 12A-12F the foot hole 232 does not have to be totally bounded by the foot base element 230, such as where the foot base element 230 is formed from two strip-like forms on either side of the foot hole 232 that are not connected to each other at their distal ends, so that the foot base element 230 is open at its distal end.

Figures 13A, 13B, 13D, 13F:
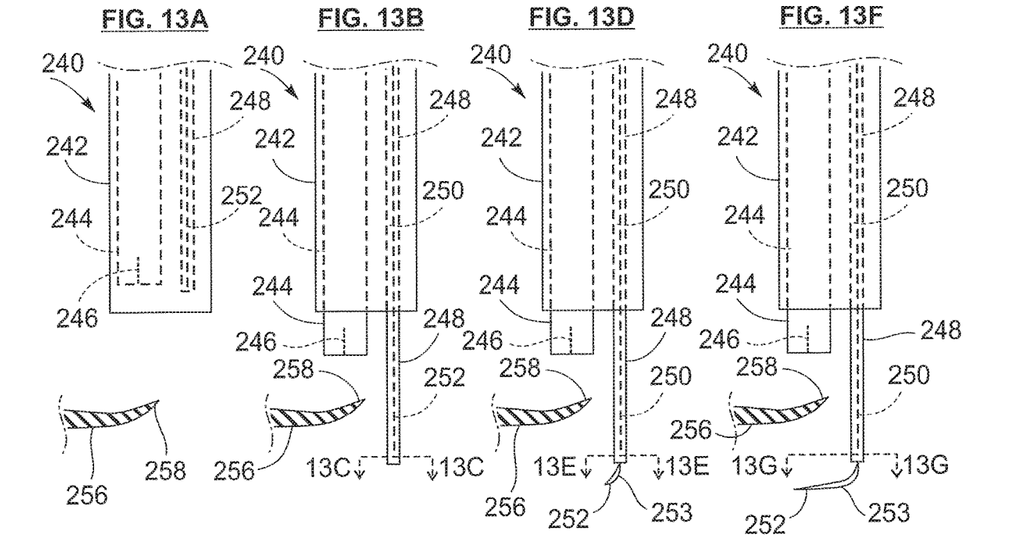
FIGS. 13A-13H depict side, side, top (sectional), side, top (sectional), side, top (sectional), and side views of a device according to an embodiment of the invention.
Figure 13C:
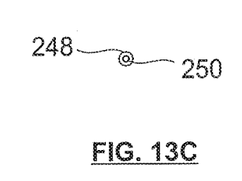
Figure 13E:
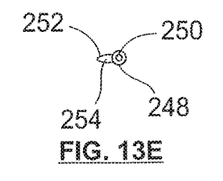
Figure 13G:
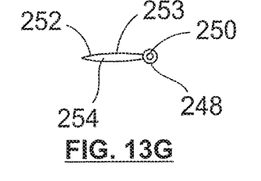
Figure 13H:
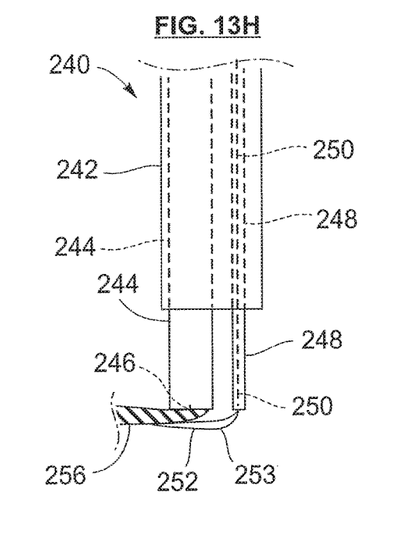

A foot element may be formed from a memory material, such as nitinol, and preset (e.g., when exposed to human temperature such as when exposed to blood flow within a heart) to assume a desired foot shape. One such embodiment is depicted in FIGS. 13A-13H, where a device 240 has a steerable catheter 242, a cutting element sheath 244 and cutting element 246, and with a foot base element 252 that has a preset memory form shape. The foot base element 252 comprises a memory-form loop 253 surrounding and defining a foot hole 254 configured when expanded to receive the cutting element 246. The foot base element 246 is positioned at the distal end of a flexible elongated foot control rod 250, and the foot base element 252 and foot control rod 250 may be formed as a single piece of nitinol or other material. During the delivery configuration depicted in FIG. 13A, the foot base element 252 is mechanically held in a radially compressed configuration by a hollow sheath 248. The steerable catheter 242 is advanced to a position adjacent a heart valve leaflet 256 to be treated, and the hollow sheath 248 is advanced from the steerable catheter 242 to a desired position, such as a position adjacent a valve leaflet edge 258 as depicted in FIGS. 13B-13C. As the foot base element 252 is advanced distally from the hollow sheath 248, the base foot element 252 begins to expand to assume its preset memory form, as depicted in FIGS. 13D-13E. With the foot base element 252 advanced fully from the hollow sheath 248, the loop 253 assumes its preset memory form to define a foot hole 254 and provide a form that can interact with the valve leaflet 256 as desired, as shown in FIGS. 13F-13G. Note that the expanded preset form of the base foot element 252 is perpendicular to the elongated foot rod 250 and extends under the distal side of the valve leaflet 256. The foot base element 252 is then moved proximally (e.g., by proximal retraction of the elongated foot rod 250) and into contact with the distal surface of the valve leaflet 256, and the cutting element sheath 244 can be advanced distally into engagement with the proximal surface of the valve leaflet 256, as depicted in FIG. 13H. The valve leaflet 256 can thus be held between the foot base element 250 and cutting sheath 244. The cutting element 246 can then be moved through the valve leaflet 236 to make the desired cuts.

Note that embodiments similar to that of FIGS. 13A-13H may be made of non-memory materials, such as stainless steel, and/or may be an open form (e.g., formed by a pair of strip-like elements that extend on either side of but do not fully enclose the foot hole) as opposed to the closed loop 253 of FIGS. 13A-13H.

The desired dimensions (e.g., length and/or width and/or shape) of the foot base element of devices of the invention depend on the particular application, including factors such as the dimensions of the native valve annulus and the dimensions of the native heart valve leaflets being bisected, as well as the particular cuts being made to the native heart valve leaflets. For example, if the foot length is too short, the length of the cuts the device can provide will be relatively short. If the foot is too long, mobility of the device within the operational space (e.g., the native valve annulus) may be reduced.

Figure 14:
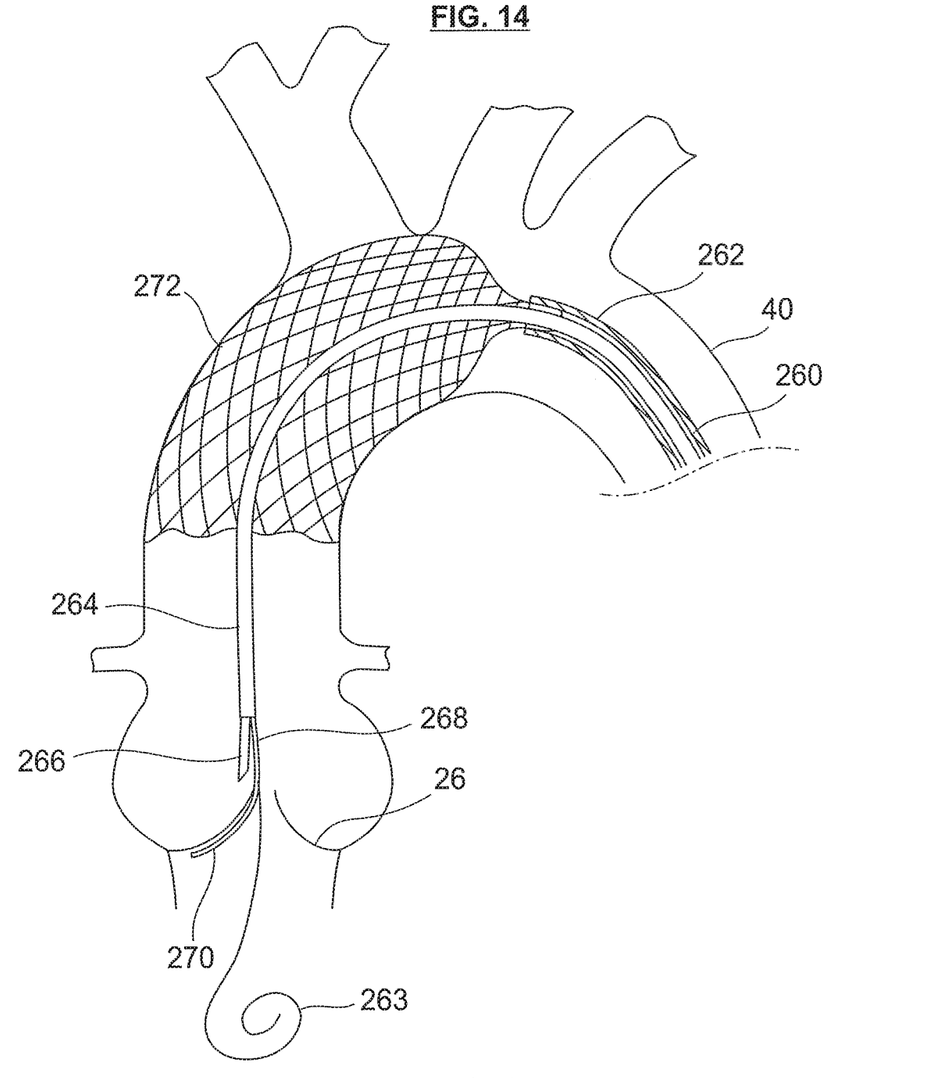
FIG. 14 depicts a side view of a heart with the device operating therein according to an embodiment of the invention.

Systems according to the invention may include embolic protection elements. For example, as depicted in FIG. 14, a device 260 has a steerable catheter 262 advanced into the aorta 26 along a guidewire 263 to a position adjacent the aortic valve 26, with a cutting element 266 extendable from the cutting element sheath 264, and with a foot 270 on a foot sheath 268 extending out of the catheter 262. The device 260 includes an embolic protection filter 272 that can be slidingly advanced and retracted from the catheter 262. The embolic protection filter 272 when extended from the catheter 262 can be expanded outward against the blood vessel and/or organ walls (e.g., the aortic wall) in order to capture any lose materials that may be dislodged during cutting of the valve leaflet.

The embolic protection filter 272 can be deployed prior to cutting of the native leaflet. Once the cutting of the native leaflet is completed, the filter 272 can be retrieved, such as by being retracted within the catheter 262, with any emboli held within the filter 272. Note that embolic protection filters such as that depicted in FIG. 14 may be incorporated into the same device/catheter as the cutting element and foot, and/or may be a separate catheter.

Figure 15:
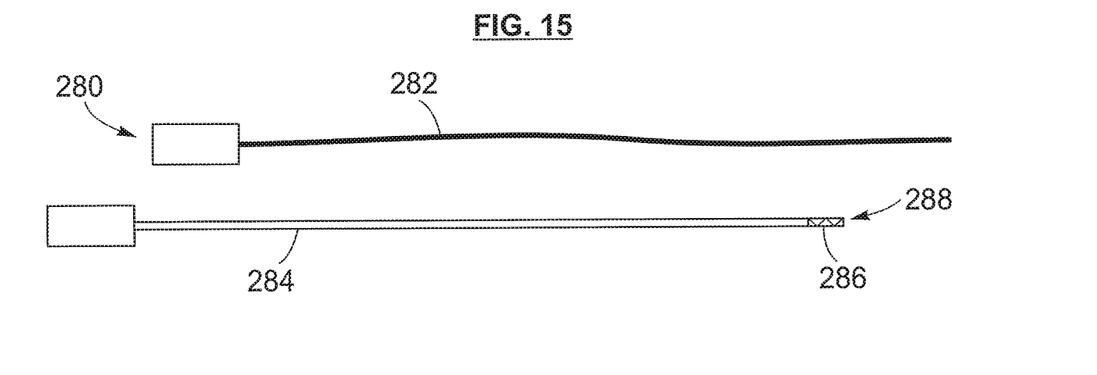
FIG. 15 depicts a side view of a system according to an embodiment of the invention.

FIG. 15 depicts a system 280 for deploying a prosthetic heart valve 286 in a patient according to an embodiment of the invention, where a leaflet cutting catheter 282 (e.g., such as that depicted in FIGS. 5-14) is used with a heart valve deployment catheter 284 having a prosthetic heart valve 286 positioned at a valve holding portion 288 of the catheter 284. The prosthetic heart valve 286 may be radially expandable, such as radially self-expanding (e.g., with a nitinol support frame) or radially balloon expandable (e.g., a stainless steel or cobalt-chromium support frame). The catheter 284 may be a balloon catheter, e.g., having a balloon at the valve holding portion 288 to radially expand the prosthetic heart valve 286.

Note that each element of each embodiment disclosed herein can be used with any other embodiment disclosed herein. For example, alignment magnets such as the magnets (110, 112) discussed with respect to the embodiment of FIGS. 5A-5D may be incorporated into each of the other embodiments of the invention. Radiopaque markers or other visibility-enhancing markers may be included with the device in order to make the device and key elements thereof more clearly visible when the device is deployed or inspected using fluoroscopy or other visualization techniques. For example, enhanced visibility markers such as radiopaque markers may be secured to portions of the sealing element and/or the anchor elements, etc.

Note that the dimensions and shape of the device and its elements depend on the particular application. For example, the dimensions and shape of the foot depend on the particular foot design and the cutting elements involved. A relatively narrow and long foot (e.g., 0.3 to 0.8 cm/less than 1 cm overall width, and 0.5 to 2.0 cm overall length) may be used where the foot is a mechanically-extended foot such as depicted in FIGS. 12A-12F, while a wider foot (e.g., 1.0 to 2.0 cm; up to 1.5 cm; up to 2.0 cm in overall width) may be used for a nitinol or similarly extendable wire-like foot (such as depicted in FIGS. 13A-13H). Also, for mechanical cutting elements such as blades and rotating rods, a smaller foot width (e.g., 0.3 to 0.8 cm/up to 1.0 cm overall width) may provide better stability and avoid tissue stretching. However, for laser and electrocautery cutting, a wider foot (e.g., 1.0 to 2.0 cm; up to 1.5 cm; or up to 2 cm overall width) may be desired in order to engage a broader surface area of the leaflet for improved leaflet holding during cutting applications.

All dimensions listed are by way of example, and devices according to the invention may have dimensions outside those specific values and ranges. Although the specific embodiments have are discussed above for use for aortic valve leaflet bisection, embodiments of the invention may also be applicable for use in bisecting valve leaflets of other heart valves, including the mitral, tricuspid, and pulmonary valves.

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A device for bisecting heart valve leaflets, comprising:
a steerable catheter shaft;
a foot sheath slidingly disposed within the steerable catheter shaft;
a foot element at a distal end of the foot sheath, the foot element configured to engage a valve leaflet, the foot element comprising a foot opening;
a foot alignment magnet disposed at the foot element;
a cutting element sheath slidingly disposed within the steerable catheter, the cutting element sheath comprising a cutting element sheath distal end;
a cutting element alignment magnet at the cutting element sheath distal end; and
a cutting element selectively extendable from the cutting element sheath distal end and into the foot opening.

2. The device of claim 1, wherein the foot element is configured when extended distally from the catheter shaft to extend sideways from the foot sheath.

3. The device of claim 2, wherein the foot element comprises nitinol.

4. The device of claim 1, wherein the foot element when extended distally from the steerable catheter shaft comprises an overall length of 0.5 to 2 centimeters.

5. The device of claim 1, wherein the cutting element comprises a motor-driven rotating rod having an abrasive surface.

6. The device of claim 1, wherein the cutting element comprises an electrocautery device.

7. The device of claim 1, wherein the cutting element comprises a curved blade.

8. The device of claim 1, wherein the cutting element comprises scissors.

9. The device of claim 1, wherein the foot alignment magnet and cutting element alignment magnet comprise one or more electromagnets.

10. The device of claim 1, further comprising an embolic filter configured to be extended from the steerable catheter shaft.

11. A system for treating a heart valve, comprising:
a device for cutting a valve leaflet as in claim 1,
a delivery catheter for delivering a prosthetic heart valve, the delivery catheter comprising a flexible elongated delivery shaft with a delivery shaft distal end, the delivery catheter further comprising a prosthetic heart valve holding portion on the delivery shaft distal end; and
a prosthetic heart valve.

12. The system of claim 11, wherein the prosthetic heart valve is held by the prosthetic heart valve holding portion of the delivery catheter.

13. The system of claim 11, wherein the prosthetic heart valve is radially expandable.

14. The system of claim 13, wherein the prosthetic heart valve is a radially self-expanding prosthetic heart valve.

15. The system of claim 13, wherein the prosthetic heart valve is balloon expandable, and the delivery catheter comprises an expandable balloon at the delivery shaft distal end.

* * * * *